United States Patent [19]

Dahlberg

[11] Patent Number: 4,996,390
[45] Date of Patent: Feb. 26, 1991

[54] NOVEL INTERSPECIFIC MUSHROOM STRAINS

[75] Inventor: Kurt R. Dahlberg, Napoleon, Ohio

[73] Assignee: Campbell Soup Company, Camden, N.J.

[21] Appl. No.: 298,727

[22] Filed: Jan. 19, 1989

[51] Int. Cl.$^5$ ............................................. A01H 15/00
[52] U.S. Cl. ........................................ 800/220; 47/1.1; 47/58; 800/DIG. 8
[58] Field of Search ............. 800/1, 220, 230, DIG. 8; 47/1.1, 58; Plt./89

[56] References Cited

U.S. PATENT DOCUMENTS 4,242,832  1/1981  Edger et al. ............................ 47/58
4,608,775  10/1986  Elliott et al. ............................ 47/58

FOREIGN PATENT DOCUMENTS 57-29229  7/1980  Japan ..................................... 800/1

OTHER PUBLICATIONS

Royse et al., "Use of Isozyme Variation to Identify Genotypic Classes of *Agaricus brunnescens*", Mycologia (1982), 74, pp. 93–102.

May et al., "Confirmation of Crosses Between Lines of *Agaricus brunnescens* by Isozyme Analysis", Exp. Mycology (1982), 6, 283–292.

Hintz et al., "The Mitochondrial DNAs of Agaricus: Heterogeneity in *A. bitorguis* and Homogeneity in *A. brunnescens*", Curr. Genetics (1985), 9, 127–132.

Hebraud et al., "Protoplast Production and Regeneration from Mycorrhizal Fungi and Their Use for Isolation and Mutants", Can. J. Microbiol (1988), 34, 157–161.

Hintz et al., "Nuclear Migration and Mitochondrial Inheritance in the Mushroom *Agaricus bitorquis*", Genetics (1988), 119, 35–41.

Loftus et al., "DNA Polymorphisms in Commercial and Wild Strains of the Cultivated Mushroom, *Agaricus bisporus*", Theor. Appl. Genet. (1988), 76, 712–718.

Royse et al., "Genetic Relatedness and Its Application in Selective Breeding *Agaricus brunnescens*", Mycologia (1982), 74, 569–575.

Abe et al., "Regeneration and Fusion of Mycelial Protoplasts of *Tricholoma matsutake*", Agric. Biol. Chem. (1982), 46, 1955–1957.

Fritsche, "Breeding *Agaricus bisporus* at the Mushroom Experimental Station, Horst", The Mushroom Journal, Feb. 1983, pp. 49–54.

Elliot, "The Genetics and Breeding of Species of Agaricus", in Flegg, et al., eds., The Biology and Technology of the Cultivated Mushroom, John Wiley and Sons, 1985, pp. 111–139.

Reymond et al., "Recombination Following Protoplast Fusion of Penicillium Strains Used in the Dairy Industry", Enzyme Microb. Technol. (1986), 8, 41–44.

Yoo et al., "Genetic Analysis of the Life Cycle in Interspecific Hybrids of *Pleurotus ostreatus* and *Pleurotus florida* Following Protoplast Fusion". Kor. J. Mycol. (1986), 14, 9–15.

Anderson et al., "Breeding Relationships Among Several Species of Agaricus", Can. J. Bot. (1984), 62, 1884–1889.

(List continued on next page.)

*Primary Examiner*—James R. Feyrer
*Attorney, Agent, or Firm*—Banner, Birch, McKie & Beckett

[57] ABSTRACT

This invention provides strains of commercial mushrooms whose genetic material comprises genes from more than one species. These strains include a novel strain of the commercial mushroom genus *Agaricus* which is a cellular hybrid produced by fusion between protoplasts of two different *Agaricus* species. In another embodiment, this invention provides improved strains for commercial production of mushroom fruit which are progeny from crosses of *Agaricus* sp. with a cellular hybrid produced by fusion between protoplasts of two different species of the genus *Agaricus*.

2 Claims, 5 Drawing Sheets

OTHER PUBLICATIONS

Toyomasu et al., "Fruit Body Formation of the Fusion Products Obtained on Interspecific Protoplast Fusion Between Pleurotus Species", Agric. Biol Chem. (1987), 51, 2037–2040.

Sonnenberg et al., "Heterokaryon Formation in the Basidiomycete *schizophyllum* Commune by Electrofusion of Protoplasts", Theor. Appl. Genet. (1987), 74, 654–658.

Peberdy, "Developments in Protoplast Fusion in Fungi", Microbiol. Sci. (1987), 4, 108–114.

Castle et al., "Restriction Fragment Length Polymorphisms in the Mushrooms *Agaricus brunnescens* and *Agaricus bitorquis*", Appl. Environ. Microbiol. (1987), 53, 816–822.

Castle et al., "Crosses Among Homokaryone from Commercial and Wild-Collected Strains of the Mushroom *Agaricus brunnescens* (=*A. bisporus*)", Appl. Environ. Microbiol. (1988), 54, 1643–1648.

Boissonnet-Menes, "Les Protoplastes de Champignons", Mushroom Science (1978), pp. 27–30.

Kawasumi et al., "High Yield Preparation of *Lentinus edodes* (Shiitake) Protoplasts with Regeneration Capacity and Mating Type Stability", Agric. Biol. Chem. (1987), 51:1649–1656.

Kiguchi et al., "Intraspecific Heterokaryon and Fruit Body Formation in *Corpinus macrorhizus* by Protoplast Fusiion of Auxotrophic Mutants", Appl. Microbiol. Biotechnol. (1985), 22:121–127.

Lee et al., "Isolation of Auxotrophic Mutants from Basidiospores of *Pleurotus conrnucopiae*", Kor. J. Mycol. (1986), 14:185–188.

Magae et al., "Electrofusion of Giant Protoplasts of *Pleurotus cornucopiae*", Appl. Microbiol. Biotechnol. (1986), 24:509–511.

May et al., "Linkage Relationships of 19 Allozyme Encoding Loci within the Commercial Mushroom Genus Pleurotus", Genome (1988), 30:888–895.

Ohmasa, "Intraspecific Protoplast Fusion of *Pleurotus ostereatus* Using Auxotrophic Mutuants", Japan J. Breed. (1986), 36:429–433.

Ohmasa et al., "Preparation and Culture of Protoplasts of Some Japanese Cultivated Mushrooms", Bull. For. & For. Prod. Res. Inst. (1987), No. 343, pp. 155–170.

Santiago, Jr., "Intraspecific Hybridization of *Volvariella volvacea* by Protoplast Fusion Technique", Phillipine J. Sci. (1983), 112:161–179.

Santiago, Jr., "Genetic Modification in *Volvariella volvaces* by Fusion of Somatic Protoplasts", Phillipine J. Sci. (1984), 113:173–190.

Sonnenberg et al., "An Efficient Protoplasting/Regeneration System for *Agaricus bisporus* and *Agaricus bitorquis*", Curr. Microbiol. (1988), 17:285–291.

Spear et al., "Formation, Purification, and Regeneration of Protoplasts from *Agaricus brunnescens*", Phytopathology (1983), 73:375.

Toyomasu et al., "Interspecific Protoplast Fusion between *Pleurotus ostreatus* and *Pleurotus salmoneo-stramineus*", Agric. Biol. Chem. (1986), 50:223–225.

Toyomasu et al., "Intra- and Interspecific Protoplast Fusion between Some Pleurotus Species", Agric. Biol. Chem. (1987), 51:935–937.

Yanagi et al., "Genetic Analyses of *Coprinus cinereus* Strains Derived through Intraspecific Protoplast Fusion", Agric. Biol. Chem. (1988), 52:281–284.

Yoo et al., "Isolation of Auxotrophic Mutants from Protoplasts of *Pleurotus ostreatus* and *Pleurotus florida*", Kor. J. Mycol. (1985), 13:75–78.

Dickhardt, "Homokaryotization of *Agaricus bitorquis* (Quel.) Sacc. and *Agaricus bisporus* (Lange) Imb.", Theor. Appl. Genet. (1985), 70:52–56.

Abe et al., "Regeneration of Mycelial Protoplasts from *Lyophyllum shimeji*", Agric. Biol. Chem. (1984), 48:1635–1636.

deVries et al., "Release of Protoplasts from Schizophyllum Commune by a Lytic Enzyme Preparation from *Trichoderma viride*", J. Gene Microb. (1972), 73:13–22.

deVries et al., "Release of Protoplasts from Schizophyllum Commune by Combined Action of Purified delta-1,3-Glucanase and Chitinase Derived from *Trichoderma viride*", J. Gene. Microbiol. (1973), 76:319–330.

Go et al., "Protoplast Formation, Regeneration and Reversion in *Pleurotus ostreatus* and *P. sajor-caju*", Kor. J. Mycol. (1985), 13:169–177.

Iijima et al., "A Method for the High Yield Preparation of and High Frequency Regeneration of Basidiomycete, *Pleurotus ostreatus* ('Hiratake'), Protoplasts Using Sulfite Pulp Waste Components", Agric. Biol. Chem. (1986), 50:1855–1861.

OTHER PUBLICATIONS

Kropp et al., "Formation and Regeneration of Protoplasts from the Ectomycorrhizal Basidiomycete Laccaria bicolor", Can. J. Bot. (1985), 64:1224-1226.

Lee et al., "Protoplast Regeneration and Reversion in *Pleurotus cornucopiae*", Kor. J. Mycol. (1986), 14:215-224.

Lee et al., "Studies on Protoplast Isolation of *Pleurotus cornucopiae*", Kor. J. Mycol. (1986), 14:141-148.

Moriguchi et al., "Preparation and Regeneration of Protoplasts from Mycelia of *Morchella esculenta*", Agric. Biol. Chem. (1985), 49:2791-2793.

Morinaga et al., "Formation and Regeneration of Protoplasts in *Coprinus pellucidus* and *Coprinus cinereus*", Agric. Biol. Chem. (1985), 49:523-524.

Mukherjee et al., "Mutagenesis of Protoplasts and Regeneration of Mycelium in the Mushroom *Volvariella volvacea*", Appl. Envir. Microbiol. (1986), 52:1412-1414.

Santiago, "Production of Volvariella Protoplasts by Use of Trichoderma Enzyme", Mushroom Newsletter for the Tropics (1982), 3:3-6.

Santiago, "Protoplast Isolation in the Common Tropical Mushroom Using Microbial Enzyme", Philipp. J. Biol. (1982), 11:365-371.

Schulz-Weddigen, "Protoplasten aus Basidien und Vegetativen Zellen von Coprinus Radiatus", Ber. Deutsch. Bot. Ges. Bd. (1982), 95:431-440.

Soon-Woo et al., "Formation and Regeneration of Protoplasts in *Lentinus edodes*", Mushroom Newletter for the Tropics (1985), 5:4-10.

Yanagi et al., "An Efficient Method for the Isolation of Mycelial Protoplasts from *Coprinus macrorhizus* and Other Basidiomycetes", Appl. Microbiol. Biotech. (1984), 19:58-60.

Yoo et al., "Studies on Protoplast Regeneration and Reversion of *Pleurotus ostreatus* and *Pleurotus florida*", Kor. J. Mycol. (1985), 13:79-82.

Yu et al., "Effects of Osmotic Stabilizers on the Activities of Mycolytic Enzymes Used in Fungal Protoplastt Liberation", Mircen J. (1987), 3:161-167.

Wakabayashi et al., "Formation of Giant Protoplasts from Protoplasts of *Pleurotus cornucopiae* by the Cell Wall Lytic Enzyme", Appl. Microbiol. Biotechnol. (1985), 21:328-330.

Wessels et al., "Reversion of Protoplasts from Dikaryotic Mycelium of Schizophyllum commune", Protoplasma (1976), 89:317-321.

Raper, "Sexuality and Life-Cycle of the Edible, Wild *Agaricus bitorquis*", J. Gen. Microbiol. (1976), 95:54-66.

Yoo et al., "Characteristics of Fusion Products Between *Pleurotus ostreatus* and *Pleurotus florida* Following Interspecific Protoplast Fusion", Korean J. Mycol. (1984), 12:164-169.

Hilber, "Valid, Invalid and Confusing Taxa of the Genus Pleurotus", Mushroom Science (1989), 12 (Part II):241-248.

Emmons et al., "Protoplasts from *Agaricus bitorquis* and *Agaricus bisporus*", Presented at the International Symposium Scientific and Technical Aspects of Cultivating Edible Fungi (1986), Abstract #27.

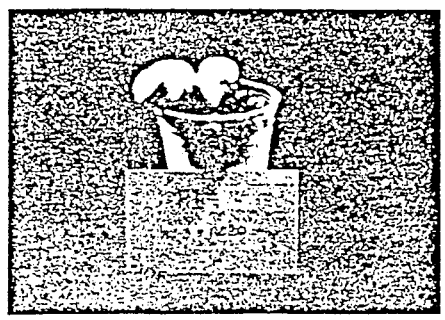

NOVEL INTERSPECIFIC MUSHROOM STRAINS

FIELD OF INVENTION

This invention relates to new strains of edible mushrooms containing genetic material from other mushroom species and having improved characteristics for commercial production.

BACKGROUND OF THE INVENTION

Commercial mushrooms grow with dikaryotic mycelia; that is, cells have two nuclei present, usually of different, compatible mating types. This is beneficial, since the presence of two nuclei of different mating types is required before fruiting for spore production will occur, and commercial mushroom strains can produce the fruiting bodies needed for sale without concern about mating efficiency during the production stage.

The commercial mushroom *Agaricus bisporus* (also called *A. brunnescens*) produces heterokaryotic spores, which means the spores contain two nuclei, so mycelia grown from spores of this species can produce fruiting bodies without any need for prior mating with another strain. In other words, this mushroom species is self-fertile. The result of this reproductive strategy is inbreeding, because there is no reproductive need for sexual crossing with another strain that might have different genetic characteristics. The organism gains no advantage from mating with another organism of differing genotype, since it is capable of producing spores using the pair of nuclei already present. This ability results in a decreased incidence of genetic recombination, which in turn results in a lower number of new genotypes than are produced by other species.

Commercial strains of this mushroom have extremely few genotypes—in the work reported by Royse, et al. (Mycologia, 74:93-102, 1982), only five distinct genotypes were found among a sample of 34 commercial mushroom strains. Castle, et al. (Appl. Environ. Microbiol., 53:816-822, 1987), also found extreme limitation in the number of genotypes present in a selection of commercial mushroom strains; they even suggested that recessive lethal alleles in one of the two nuclei present, which would be masked by the alleles of the other nucleus, may account for part of the limitation in outcrossing that occurs among commercial mushroom strains.

The low level of genetic diversity within commercial mushroom strains was originally detected by Royse, et al. (1982), using isozyme analysis. By means of this analysis these workers were able to identify homokaryotic strains, those having only one nuclear type, and they were able to produce crosses between different homokaryotic strains. Castle, et al. (1987, above, and Appl. Environ. Microbiol., 54:1643-1648, 1988), extended this type of study by means of restriction fragment length polymorphism (RFLP) analysis which gave an improved ability to identify genotypes and to detect successful crosses, based on the presence of alleles from one or both putative parents.

One approach to the development of improved strains for commercial production is disclosed by Eger et al., in U.S. Pat. No. 4,242,832, where these workers proposed the isolation of a collection of monokaryotic strains, which can be characterized as to their genetic makeup and then mated in desired pairs to produce a desired genotype in the resultant dikaryote. This approach is limited by the range of genetic variability within the existing genotypes present in the strains used for mating, which is a severe limitation for the strains used in commercial mushroom production. Elliot, et al., U.S. Pat. No. 4,608,775, teaches a procedure for increasing genetic diversity by classical mutagenesis, using homokaryotic strains subjected to mutagens such as ultra-violet light, followed by mating of the mutated strains. While he was successful in a particular instance involving resistance to fungicides, work of this type is tedious and technically difficult, with limited potential for improvement within the species.

The genus Agaricus contains a number of species apart from *A. bisporus*, the species used for commercial mushroom production. These other species have different morphological and growth characteristics. For example *A. bisporus* can be morphologically distinguished from *A. bitorquis*, because *A. bisporus* has round caps, moderate length stipes and a single annular ring around the stipe, while *A. bitorquis* has flattened caps, short stipes and a double annulus. Whereas *A. bisporus* has an optimum growth temperature of 25-27 C. and a maximum growth temperature of 29-30 C., *A. bitorquis* has an optimum growth temperature of 30 C. and a maximum growth temperature of 34-35 C. These gross differences between the two species are, of course, the result of differences in the enzyme composition, and ultimately the genetic makeup of the species.

A potential source of genetic diversity to use in development of improved commercial mushroom strains could be the related but distinct genes of other species in the genus Agaricus. However, Anderson, et al. (Can. J. Bot., 62:1884-1889, 1984), reported that matings of homokaryotic Agaricus mushroom strains were successful within a given species, but were unsuccessful between different species of the same genus. This prevents the introduction of diversity from related species.

A method used in other organisms to introduce genetic diversity is protoplast fusion using protoplasts of two different species. The use of this technique in fungi has been reviewed by Peberdy (Microbiol. Sci., 4:108-114, 1987). First, protoplasts are prepared by enzymatically dissolving the cell walls of the fungi in a medium of high osmotic strength. Then protoplasts from two strains are mixed in the presence of polyethylene glycol and calcium ion. The fused protoplasts are transferred to a new growth medium in which normal cell morphology is regenerated. Some of the resultant cells have genetic material from both of the parent strains. In order to select for fusion products of both parent stains, these experiments are often done using parent strains which are auxotrophic for different nutrients. Subsequent use of minimal growth medium prevents regeneration of protoplasts from the auxotrophic parents, and only fusion products with complimentary genetic capability resulting in prototrophy will grow. Peberdy reports a number of crosses in yeast between different species that were achieved by means of protoplast fusion.

Successful interspecies fusion has also been reported for fungi imperfecti. Reymond, et al. (Enzyme Microb. Technol., 8:41-44, 1986), used auxotrophic strains of Penicillium in a search for improved fungi to use in cheese-making. He reported a number of successful intraspecies fusions. He also reported sucessful interspecific fusion between *P. caseicolum* and *P. album*; however interspecies fusion between *P. roqueforti* and either of the other two Penicillium species above was never successful.

Protoplast fusion has also been reported in basidiomycetes. Sonnenberg, et al. (Theor. Appl. Genet., 74:654-658, 1987), describes fusion of protoplasts of the basidiomycete species *Schizophyllum commume* using electrofusion, in place of the more common polyethylene glycol-induced fusion. Abe, et al. (Agric. Biol. Chem., 46:1955-1957, 1982), discloses a method for intrasprecies fusion of protoplasts from *Tricholoma matsutake* using glycine-$CaCl_2$-NaCl, because polyethylene glycol is reported to rupture the protoplasts, rather than stimulate fusion. Subsequently this group reported interspecies fusion of *T. matsutake* (Japanese Patent Document 57-029229A) in which polyethylene glycol-induced fusion was used. Yoo, et al. (Kor. J. Mycol., 14:9-15, 1986), reported interspecific fusion in Pleurotus which resulted in fruiting-capable progeny. In contrast Toyomasu, et al. (Agric. Biol. Chem., 51:2037-2040, 1987), also studying Pleurotus, found that his interspecific fusion products were incapable of fruiting unless they were back-crossed with one of the parent strains to produce a new heterokaryotic strain. Castle, et al. (1987), reports preparation of protoplasts from Agaricus, the fungal genus which includes commercial mushroom strains, but insofar as the inventor of this application is aware no one has attempted fusion, either within one species or between species, in this mushroom genus.

SUMMARY OF THE INVENTION

It is an object of this invention to provide improved strains of the commercial mushroom genus Agaricus.

It is another object of this invention to increase the genetic diversity available within strains of the commercial mushrooms genus Agaricus, for the purpose of breeding new mushroom strains with improved commercial performance.

It is a further object of the invention to provide strains of commercial mushrooms whose genetic material comprises genes from more than one species.

This invention provides, in one of its embodiments, a novel strain of the commercial mushroom genus Agaricus which is a cellular hybrid produced by fusion between protoplasts of two different Agaricus species. In another embodiment, this invention provides improved strains for commercial production of mushroom fruit which are progeny from crosses of Agaricus sp. with a cellular hybrid produced by fusion between protoplasts of two different species of the genus Agaricus. In a further embodiment, this invention provides homokaryotic strains of Agaricus which contain genes from more than one species and which can be crossed with other Agaricus strains to produce fruiting-capable progeny strains for commercial production.

To develop new genotypes with phenotypic improvements in commercially important characteristics is an extremely laborious task using classical breeding techniques, because of the limited genetic diversity in this starting base. One alternate approach is to introduce new genes from other species of Agaricus, which is an objective of this invention. Anderson, et al., tried to cross different species of Agaricus by classical mating techniques, but without success. The interspecies strain of this invention was produced by protoplast fusion, using protoplasts from *A. bitorquis* and *A. bisporus* in order to achieve the objects mentioned above.

Cells regenerated from these fused protoplasts proved to be true interspecies cellular hybrids by restriction fragment length polymorphism analysis. The novel, interspecies strain, Agaricus sp. ATCC 20916, was found to be incapable of forming fruiting bodies, but it could be crossed with other mushroom strains to produce new, fruiting-capable strains. A new strain from this cross contained genetic material from both species, as demonstrated by restriction fragment length polymorphism analysis. The strains also showed unexpected hybrid vigor, including a pattern of much faster growth. Most unexpectedly, the new interspecies fruiting strains did not produce scaly caps at the first break (the first crop of mushroom caps harvested from a newly seeded bed). Instead, the new fruiting strain produced high quality mushrooms starting with the first crop.

BRIEF DESCRIPTION OF THE FIGURES

FIG. 1 is a photograph of mushroom fruit produced by the offspring of Agaricus strain ATCC 20916 and a strain of *Agaricus bitoquis*.

FIG. 2 shows the performance in fruiting trials of Agaricus interspecies hybrid strain H1 derived from the cross of Agaricus strain ATCC 20916 and *Agaricus bitorquis* strain AE20 (ATCC 64999).

(iii)

FIG. 4 shows restriction fragment length polymorphism (RFLP) analysis of representative H1 interspecies hybrid derivatives.

(iii)

DETAILED DESCRIPTION OF THE INVENTION

Figure 2A:
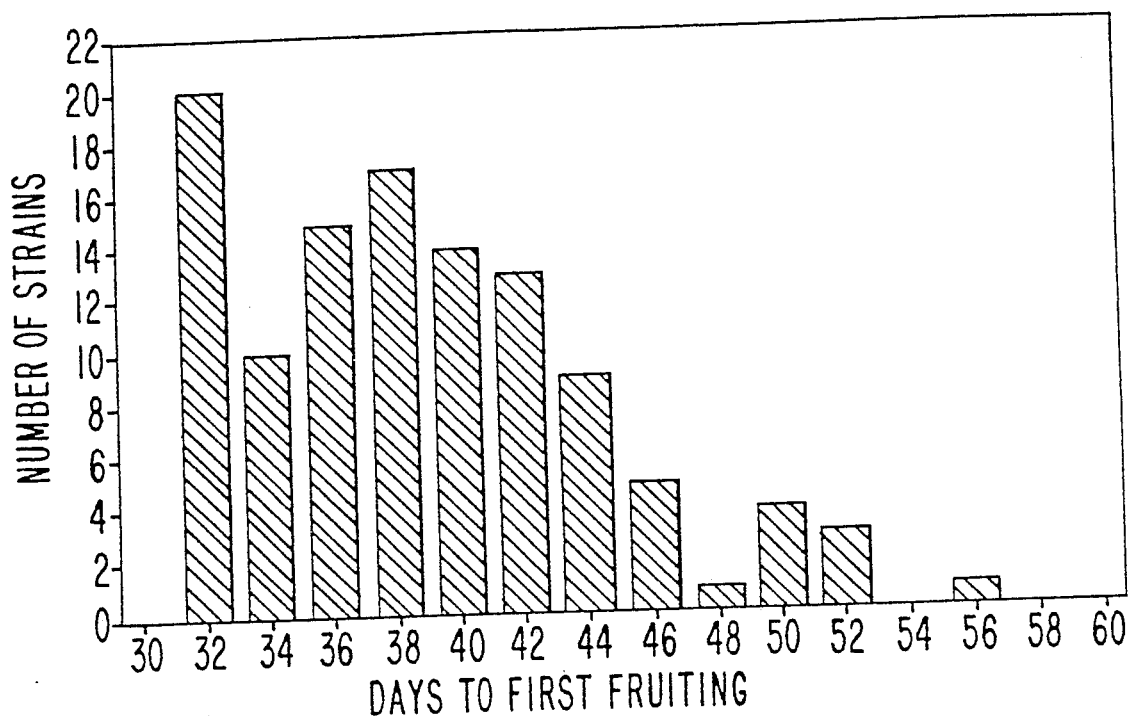
FIG. 2A shows days to fruiting vs. number of strains.

In order to introduce new diversity into the genetic pool of the commercial mushroom population, cells of the commercial mushroom species *Agaricus bisporus* can be combined with cells of another Agaricus species by protoplast fusion. Candidates for fusion are preferably selected from homokaryotic stains of Agaricus species that are auxotrophic for particular nutrients. After the fusion reaction, selection to eliminate the parent strains can be achieved by simply growing the resultant strains in the absence of the particular nutrient, because the parent strains cannot grow under these conditions. Preferred strains, which were used in the examples below, are *Agaricus bitorquis* strain AE20 (which is auxotrophic for nicotinic acid and resistant to cycloheximide and which has been deposited with the American Type Culture Collection, Rockville, Maryland, under accession number ATCC 64999) and a homokaryotic strain of the commercial species, *A. bisporus* ATCC 24662

(which is auxotrophic for adenine and uracil and resistant to cycloheximide).

Protoplasts of the selected strains can be produced by conventional protoplasting procedures; for example, the procedure described for making protoplast from cells of Agaricus species in Castle, et al. (1987) may be used. Once protoplasts of the selected strains have been prepared, fusion of the two strains can be induced by a number of methods. Most conventional procedures rely on polyethylene glycol and calcium ion; however, those skilled in the art will recognize that other chemical inducers or electrofusion procedures can also induce fusion of protoplasts.

Colonies may be regenerated from the fused protoplasts by well-known, conventional procedures for mycelial regeneration from fungal protoplasts. These procedures generally involve dilution of the protoplasts into a fungal growth medium, followed by plating on agar, with or without a cover layer of soft agar, or in the alternative dilution into a growth medium containing soft agar which is poured into petri dishes for incubation. The colonies which grow upon incubation are then selected by re-plating in a minimal growth medium in which prototrophic fusion products will grow, but regenerants from the auxotrophic parent strains will not.

In accordance with this invention, protoplasts released from *Agaricus bisporus* strain ATCC 24662 (requiring the addition of adenine and uracil to the medium for vegetative growth and being resistant to the drug cycloheximide at a concentration of 15 ug/ml) were fused with protoplasts of *A. bitorquis* strain AE20 (requiring the addition of nicotinic acid to the medium for vegetative growth and being resistant to the drug cycloheximide at 15 ug/ml), both of which had been grown in MPFYE broth. MPFYE broth contains (per liter of deionized water): malt extract, 20.0 g; peptone, 2.0 g; fructose, 20.0 g; yeast extract, 2.0 g; $KH_2PO_4$, 0.46 g; $K_2HPO_4$, 1.0 g; $MgSO_4$, 1.0 g; and Vogel's trace element solution (Vogel, American Naturalist, 98:435-446, 1964), 0.20 ml. When necessary, MPFYE broth is solidified by the addition of 15-20 g/l of bacteriological agar. Protoplasts were mixed in approximately equal ratios and treated to induce fusion.

The preferred practice for induction of fusion includes adjusting the protoplast mixture to 20% polyethylene glycol, 50 mM sodium citrate, and 100 mM $CaCl_2$ by the addition of an equal volume of 40% polyethylene glycol, 50 mM sodium citrate, and 100 mM $CaCl_2$. After a few minutes, the mixtures are adjusted to 30% polyethylene glycol by addition of the same solution. Mixtures are incubated in this solution for 30-60 min to allow fusion of protoplasts. This process allows protoplasts from the two species to aggregate and membranes to fuse, mixing the cytoplasm and nuclei from the species. The mixture of the genetic components of the protoplast types is thought to be responsible for the traits of the resulting mushroom strains.

Following protoplast fusion, mixtures were diluted in an appropriate liquid medium (such as MPFYE broth containing 0.6M mannitol or 0.6M sucrose) and spread over the surface of a petri dish containing MPFYE broth plus 30% spent MPFYE broth solidified with 1-2% agar. (Spent broth is broth in which fungi have been grown and from which the fungal mycelia has been removed.) Plates were incubated at 25°-29° C. for 3-14 days, at which time colonies appeared on the surface of the medium. Colonies represent protoplasts (unfused, homologously fused, or heterologously fused) which have resynthesized a cell wall and resumed their normal mycelial growth pattern. This process is called reversion of protoplasts or regeneration of mycelia, and occurs spontaneously, although at low frequencies under appropriate nutritional and environmental conditions. Reversion rates among Basidiomycete fungi are generally quite low, with rates of 0.1% being fairly common.

Following regeneration of mycelia, each colony can be tested for the desired genetic traits. Revertant colonies should be tested for growth on a minimal medium (such as (per liter deionized water): glucose, 20 g; asparagine or $NH_4NO_3$, 2.0 g; thiamine, 120 mg; $KH_2PO_4$, 0.46 g; $K_2HPO_4$, 1.0 g; $MgSO_4$, 0.5 g; Vogel's trace element solution, 0.2 ml; and agar, 15 g) and for the ability to grow in the presence of 15 ug/ml cycloheximide. Unfused or homologously fused *A. bisporus* strain ATCC 24662 colonies do not grow on minimal medium because of the absence of adenine and uracil, while unfused or homologously fused *A. bitorquis* strain AE20 (ATCC 64999) colonies do not grow on this medium because of the absence of nicotinic acid. Colonies arising from fused protoplasts of *A. bisporus* and *A. bitorquis* are capable of growing on the minimal medium due to the complementation of genetic markers. That is, colonies possess the ability to grow in the absence of adenine and uracil from the *A. bitorquis* strain and the ability to grow in the absence of nicotinic acid from the *A. bisporus* strain.

The cellular hybrid fusion product of *A. bisporus* strain ATCC 24662 and *A. bitorquis* strain AE20 (ATCC 64999) was deposited with the American Type Culture Collection, Rockville, Maryland, on Jan. 13, 1989, and given the accession number ATCC 20916. This strain was given the internal designation of strain HB3. Strain HB3 is distinct from the parental strains by the following criteria:

1. The strain is prototrophic. That is, it grows well on a minimal medium and shows no requirement for adenine, uracil or nicotinic acid.

2. The optimum temperature for growth of strain HB3 is intermediate between *A. bisporus* and *A. bitorquis*. Whereas *A. bitorquis* has an optimum growth temperature of 30° C. and *A. bisporus* has an optimum temperature of 25°-27° C., strain HB3 grows best at 29° C.

3. The isoenzyme patterns of strain HB3 are distinctive and show homologies with both *A. bisporus* strain ATCC 24662 and *A. bitorquis* strain AE20 (ATCC 64999). The electrophoretic pattern for the enzyme laccase is similar to the *A. bisporus* pattern, while the electrophoretic pattern for peroxidase is similar to the *A. bitorquis* pattern. (Isozyme profiles were determined by the method of Tanksley and Orton "Isozymes in Plant Genetics and Breeding," Elsevier, New York, 1983, and the laccase stain of Leslie and Leonard, Mycologia, 71:1082-1085, 1979, was used.)

4. The restriction fragment length polymorphism (RFLP) patterns of the HB3 strain were examined by the procedure of Castle, et al., Appl. Environ. Microbiol., 54:1643-1648 (1987). The RFLP patterns show that HB3 is distinguishable from the parental strains; RFLP fragments from both parents are present, and some additional fragments are also present.

*Agaricus sp.* strain HB3 is incapable of fruiting when tested under standard laboratory conditions. The preferred testing protocol is essentially as described by San Antonio (1971) in Mycologia 63:16-20. Strains to be tested are grown in 200 g of sterile rye grain (about 50% moisture content) containing about 1% CaCO₃. Following complete colonization, grain is poured into 16 oz. plastic beverage cups, and 100 g of calcined earth containing 5% CaCO₃ and 1% hydrogel is added to the surface. This layer is hydrated to its water holding capacity with deionized water, covered, and incubated at room temperature. Following growth of mycelium to the surface of this "casing layer", covers are removed and the cups are incubated at 18°–19° C., 85% relative humidity until mushrooms form. Strains grown on rye grain can also be inoculated into 100–200 g of mushroom compost for equivalent testing and/or can be cased with a peat moss/CaCO₃ mixture.

In the genus Agaricus, only heterokaryotic strains are known to form mature fruiting bodies. A heterokaryotic strain is one that contains dissimilar genetic elements present in two different nuclei. Strain HB3 can be crossed with strains of Agaricus species, such as *A. bisporus* or *A. bitorquis* strains, to form putative heterokaryotic strains. The preferred protocol for conducting crosses among homokaryotic strains is essentially as described by Castle et al. (1988). Agar plugs cut from the periphery of actively growing strains to be tested are placed approximately 1 cm apart on agar medium. The zone of confluence where the two strains grow together is removed to a fresh agar medium. Putative heterokaryons have been tested for fruiting competence as shown in the Examples according to the standard protocol described above.

The genetic complement of heterokaryotic strains which are the progeny of crosses between an interspecies strain, such as HB3, and another Agaricus strain will comprise genes from more than one species. These heterokaryotic strains can be used as a source of genetic diversity in a breeding program such as the programs described by Eger, et al., or by Castle, et al. (1987, 1988). To carry out these programs, homokaryotic strains are first isolated from heterokaryotic strains of interest, then particular homokaryotic strains are mated to produce desired heterokaryotes. Criteria for selecting the homokaryotic strains to be mated are well known in the art (see Royse, et al., Mycologia, 74:569–575, 1982; Fritsche, Mushroom J., February, 1983, pp. 49–53; Elliott, in Flegg, et al., eds., "Biology and Technology of the Cultivated Mushroom", Wiley & Sons, New York, 1985, pp. 111–129; Eger, et al.; and Castle, et al., 1987).

Homokaryotic, self sterile Agaricus strains are preferably isolated from heterokaryotic strains by protoplast methods. Agaricus protoplasts are induced to form by the methods described previously. After filtration to remove mycelial fragments and centrifugation to concentrate them, protoplasts are resuspended in MPFYE broth containing 0.6M sucrose or mannitol, adjusted to a convenient cell density (usually $1.0 \times 10^6$/ml or less), and plated on MPFYE agar containing 0.6M sucrose or mannitol. Protoplasts begin to regenerate 3 to 14+ days after plating. Relatively slow growing colonies are selected as possible homokaryons and are transferred to fresh MPFYE agar. Possible homokaryons are tested for the ability to fruit. Those that fail to fruit are considered to be probable homokaryons. The status of probable homokaryons is confirmed by additional fruiting tests or by RFLP or isoenzyme analyses. Our data show that approximately 25% of protoplasts are mononucleate, and thus have the potential to regenerate to form homokaryons. In practice, the frequency of homokaryotic protoplast regenerates is 10% or less. This method is similar to that described by Castle et al., 1987, attributed to the inventor of this application.

Those skilled in the art of breeding commercial mushrooms can mate Agaricus strains with strain HB3, or homokaryotic strains isolated from the progeny of strain HB3, in order to introduce genetic diversity from other Agaricus species into the gene pool of the commercial mushroom. The following examples report the results of mating between the interspecies, non-fruiting strain HB3 and a particular strain of another Agaricus species. These examples are intended to further illustrate the invention, not to limit the invention in any way. The invention is limited only by the scope of the appended claims.

EXAMPLE 1

Interspecies hybrid strain HB3 was crossed to a number of *A. bisporus* and *A. bitorquis* homokaryotic strains. With one noteworthy exception, none of the crosses was capable of forming a mushroom fruiting body. The one exception was a cross between strain HB3 and *A. bitorquis* strain AE20 (note that this is one of the partners in the original fusion event). The resulting mushroom was designated H1, and is shown in the photograph in FIG. 1. The H1 mushroom has the following characteristics:

1. Smooth, white cap texture.
2. *Agaricus bisporus* morphology. *A. bisporus* and *A. bitorquis* can be morphologically distinguished. *A. bisporus* mushrooms have round caps, moderate stipe lengths, and a single annular ring around the stipe. In contrast, *A. bitorquis* mushrooms have a flattened cap, short stipes, and a double annulus.
3. Predominantly two-spored basidia. *A. bisporus* has predominantly two-spored basidia, while *A. bitorquis* has fourspored basidia.

EXAMPLE 2

Basidiospores released from the H1 mushroom were collected on sterile filter paper. A sample of basidiospores was suspended in sterile deionized water, spread on the surface of a nutrient agar medium, and allowed to germinate. Colonies arising from 124 of the germinating spores were randomly selected and transferred to fresh medium. These "single spore isolates" were designated H1-001 to H1-124 (or generically as "H1-SSI"). Some of the single spore isolates "sectored" into more than one morphological growth pattern, and are given designations such as "H1-032" and "H1-032A". The total number of H1-derived strains was 128. The 128 H1-derived strains were subjected to genotype testing and were also tested for the ability to fruit under standard laboratory conditions (described above). Data from these tests are included in Table 1 and FIG. 2. Fifteen of these strains failed to fruit under laboratory conditions, and are considered to be homokaryotic. The homokaryotic nature of some of these strains has been confirmed by RFLP and/or isoenzyme testing. Note that some of the H1 homokaryotic strains show genetic traits of both parental types. A homokaryotic strain containing both parental markers could only occur after genetic recombination between the parents.

The remaining 113 strains were capable of fruiting, and are therefore considered to be heterokaryotic. One noteworthy observation among the fruiting trials is that the H1-SSI's aggressively colonized the grain substrate and rapidly grew into the casing layer. The rapidity of strain growth is apparent in FIG. 2A which gives time to fruit in laboratory tests. While the control stain *A. bisporus* M2 normally requires 45-46 days to fruit (from the time of culture inoculation) under the conditions tested, some H1-SSI strains fruited in as little as 31 days. Thus, one feature of the H1-SSI strains is their speed of growth and substrate colonization which can be observed as a shortened time between culture inoculation and the appearance of the first mushrooms.

DNA probed with the RFLP marker pAg33n25 show a range of homologies. Strain ATCC 64999 has a characteristics band at 1.4 kpb that does not exist in strain ATCC 24662. Strain ATCC 24662 has a characteristic band at 2.5 kbp that does not exist in strain ATCC 64999. H1-SSI strains H1-41, H1-80, H1-86 and H1-91, as well as strain H1-EX have both the 1.4 and 2.5 kbp bands, showing that they contain the genetic material of both parents. Similarly in FIG. 4B, with BamH1 digests

TABLE 1

Summary of data on strain H1 derivatives.

| NUMBER OF STRAINS | FRUITING COMPETENCE | AUXOTROPHIC MARKER | CYCLOHEXIMIDE RESISTANCE OR SENSITIVITY | AUXOTROPH OR PROTOTROPH |
|---|---|---|---|---|
| 1 | HOMOKARYOTIC | ???? | RESISTANT | AMBIGUOUS |
| 2 | HOMOKARYOTIC | NIC/ADE | RESISTANT | AUXOTROPH |
| 1 | HOMOKARYOTIC | NIC | RESISTANT | AUXOTROPH |
| 1 | HOMOKARYOTIC | NIC/ADE | SENSITIVE | AUXOTROPH |
| 1 | HOMOKARYOTIC | NIC/ADE/URA | SENSITIVE | AUXOTROPH |
| 9 | HOMOKARYOTIC | NONE | RESISTANT | PROTOTROPH |
| 1 | HETEROKARYOTIC | NIC | SENSITIVE | AUXOTROPH |
| 4 | HETEROKARYOTIC | NONE | UNKNOWN | PROTOTROPH |
| 68 | HETEROKARYOTIC | NONE | RESISTANT | PROTOTROPH |
| 40 | HETEROKARYOTIC | NONE | SENSITIVE | PROTOTROPH |

EXAMPLE 3

Interspecies hybrid strain H1-SSI's were evaluated in "step 2" trials for traits of potential value to commercial mushroom cultivation. A step 2 trial involves small scale commercial cultivation in duplicate 2'×2' trays filled with the equivalent of 16 lb dry weight of mushroom compost. Trays are treated as they would be under commercial conditions. The primary traits of interest are yield potential and mushroom quality (color, cap morphology, cap scaliness, etc.). The results of the initial step 2 evaluations are summarized in FIG. 2.

Figure 2B:
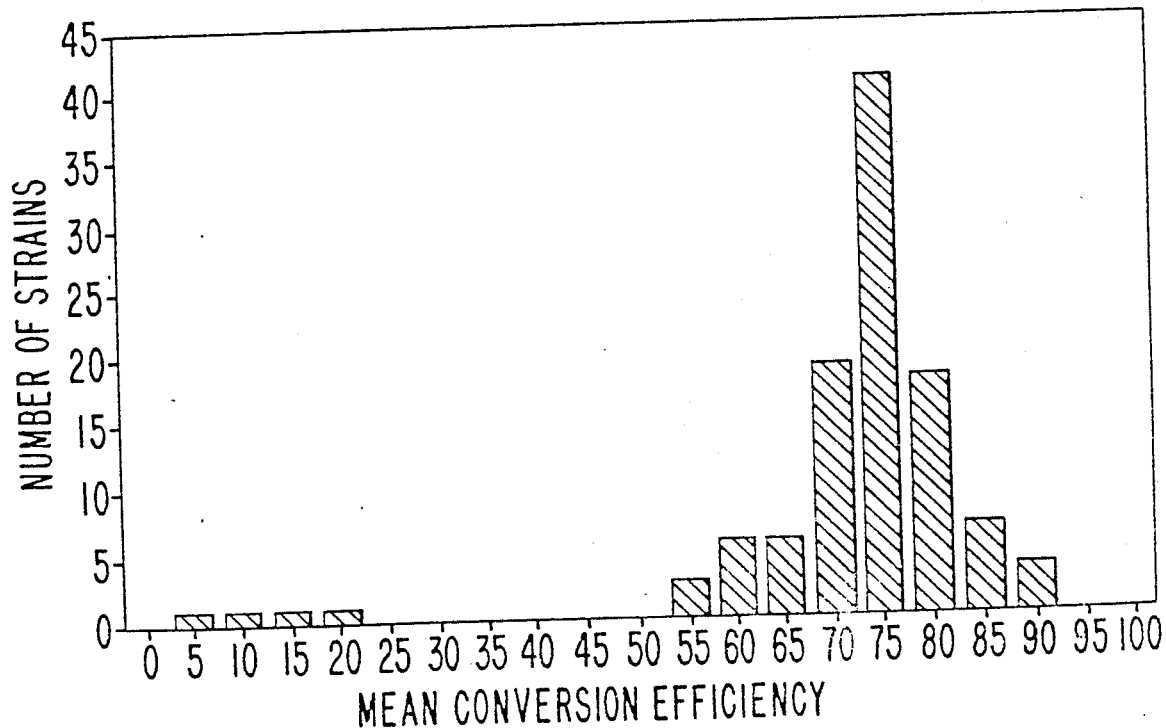
FIG. 2B shows conversion efficiency vs. number of strains.

FIG. 2B shows yield distribution of strain H1 heterokaryons in step 2 fruiting trials. Percent conversion efficiency (CE) is the fresh weight of mushrooms produced per dry weight of compost. The strain M2 control gave a conversion efficiency of 73%. Mushroom yields ranged from a low of 0.11% conversion efficiency (pounds fresh weight of mushrooms per pounds dry weight of compost) to a high of 89.13% conversion. Twenty five H1 progeny had yields exceeding those of the strain M2 control.

Figure 2C:
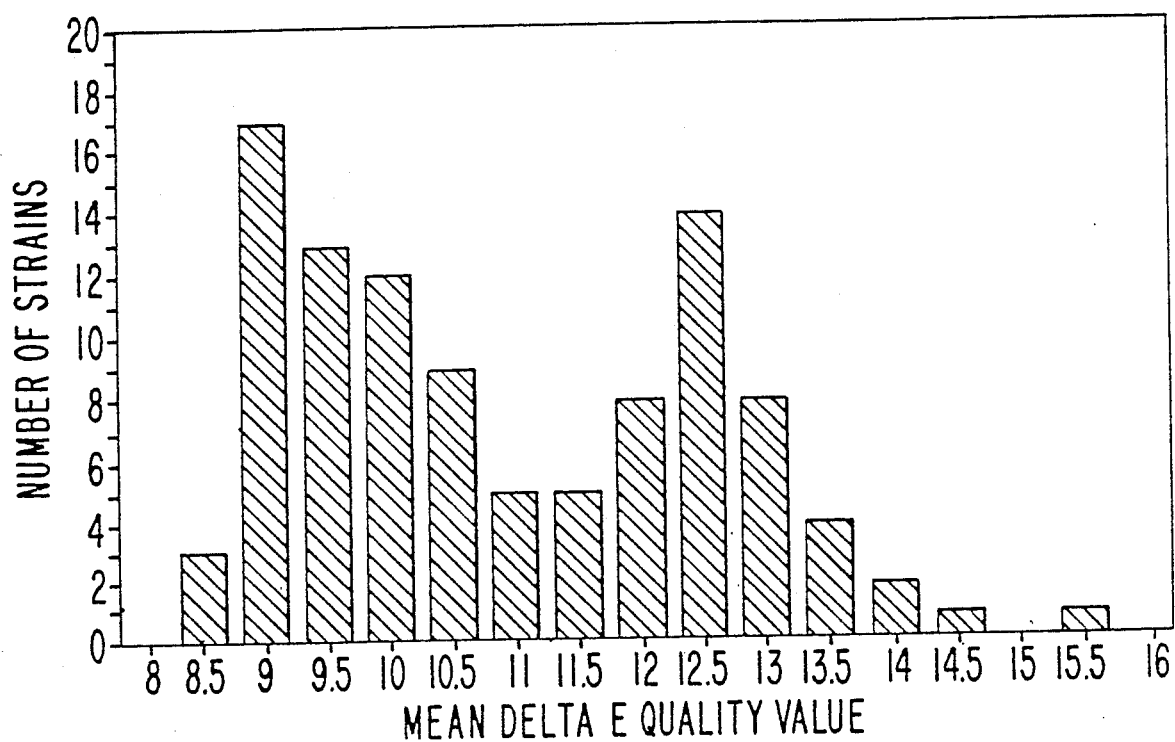
FIG. 2C shows quality value vs. number of strains.
Figure 3:
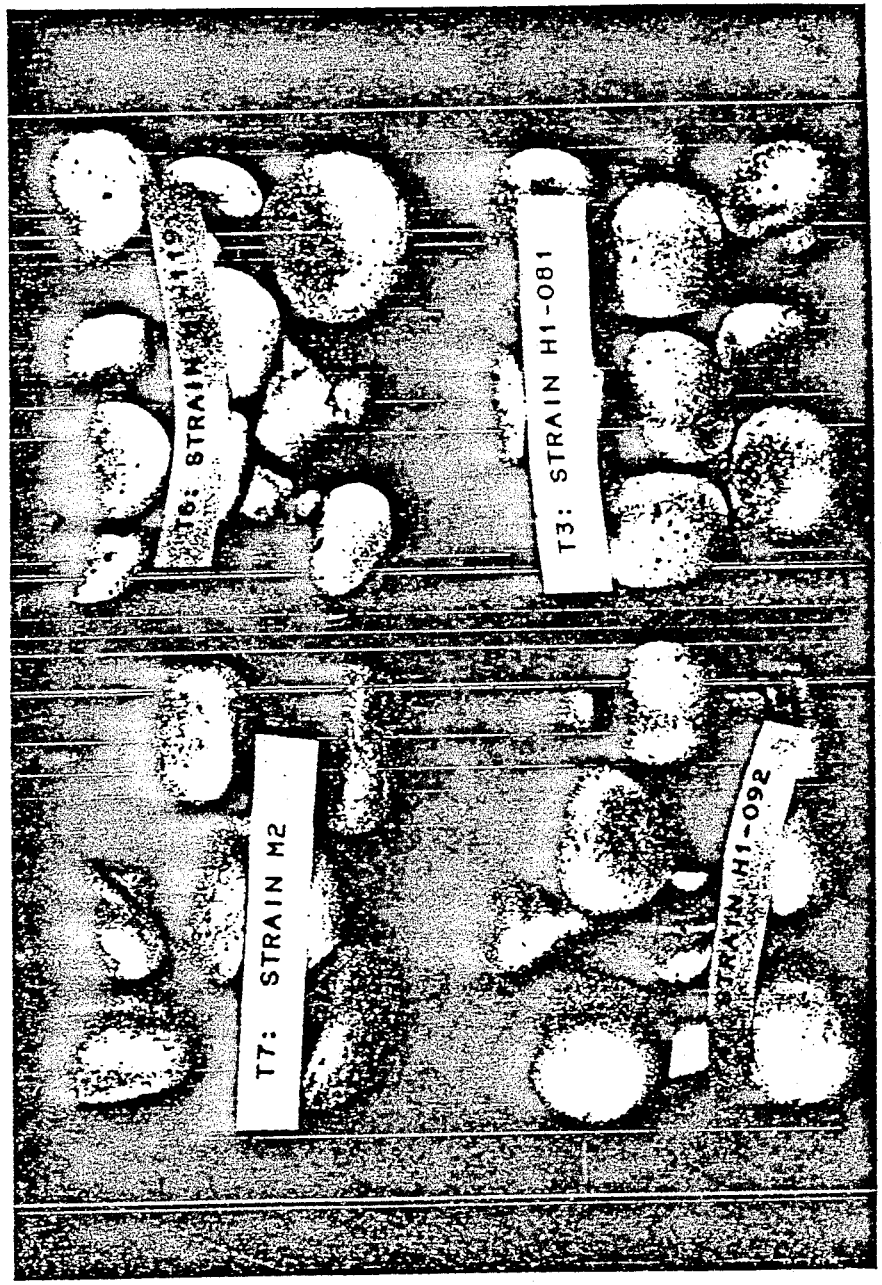
FIG. 3 is a photograph of mushrooms produced by the commercial strain M2 and by representative strains isolated by single spore culture from the offspring of Agaricus strain ATCC 20916 and a strain of *Agaricus bitorquis*.

Quality measurements (Minolta Chroma meter color readings, expressed as "delta E" values; lower delta E values reflect better mushroom quality) are summarized in FIG. 2C. Strain M2 mushrooms generally give delta E values in the range of 11-12. Several H1-SSI strains showed particularly good mushroom quality. Interestingly, strains showing the best overall yield also showed the best quality (lowest delta E values). Subjective evaluations of mushroom quality revealed that the H1-SSI strains had smooth, white, "high quality" mushrooms. Photographs of representative mushroom types are shown in FIG. 3.

EXAMPLE 4

Figure 4A:
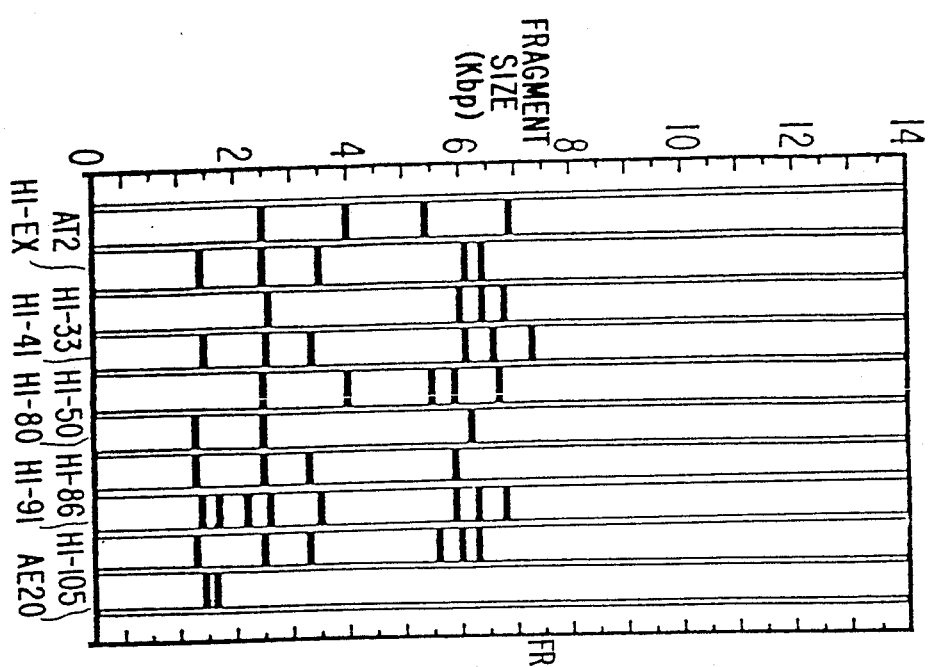
FIG. 4A shows EcoR1 digests probed with pAg33n25.
Figure 4B:
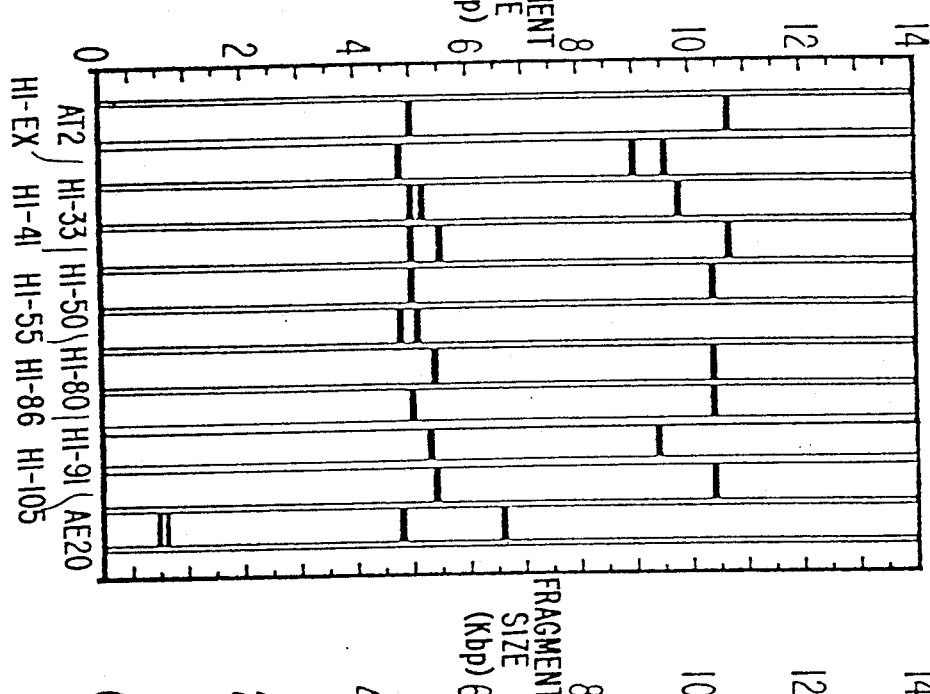
FIG. 4B shows BamH1 digests probed with pAg33n10.
Figure 4C:
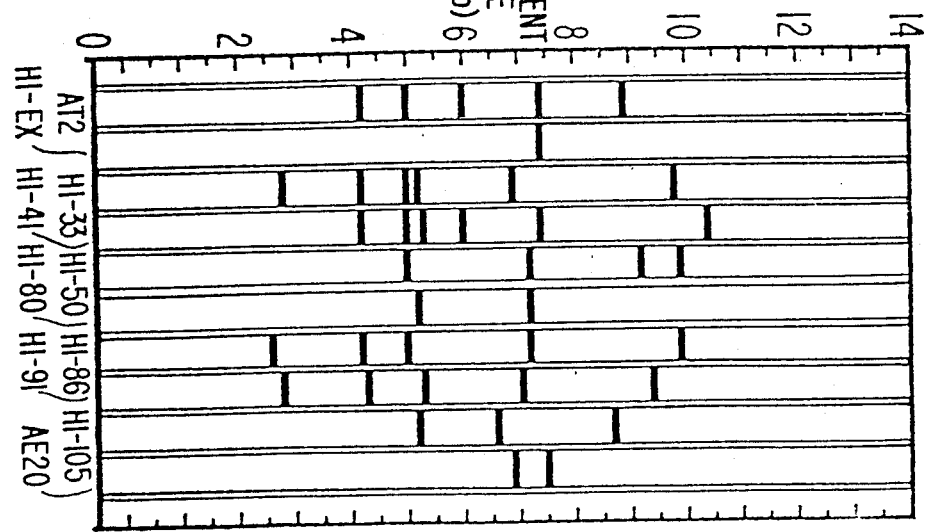
FIG. 4C shows BamH1 digests probed with pAg33n25.

Restriction Fragment Length Polymorphisms (RFLPs): H1 strains shown RFLP homologies with both *A. bisporus* and *A. bitorquis* which can be seen in FIG. 4. All procedures were as described by Castle, et al. (1987) except that RFLP probes were labelled and detected with a "Blue-Gene" biotinylation kit (BRL, Bethesda, Md). In FIG. 4A EcoR1 digests of total probed with pAg33n10, strain H1-55 shows a 4.8 kbp band characteristics of ATCC 64999 and a 5.1 kbp band characteristic of ATCC 24662. FIG. 4C shows BamH1 digests probed with pAg33n25; strain H1-33 has 4.2 and 5.0 kbp bands characteristics of ATCC 24662 and a 6.9 kbp band characteristics of ATCC 64999.

EXAMPLE 5

Isoenzyme polymorphisms: Isoenzyme polymorphism data are less conclusive than RFLP analyses because of the potential differences in enzyme expression with different cell types and the requirement that enzymes be extracted in an active state. However, the data do indicate that the H1 strains are indeed interspecies hybrids. For example, strain H1-041 has characteristic laccase bands at Rf=0.18, 0.22, 0.31, and 0.61 that correspond to the *A. bisporus* ATCC 24662 pattern and bands at ca Rf=0.45 and 0.49 that correspond to the *A. bitorquis* AE20 (ATCC 64999) pattern. Similar relationships exist for glucose oxidase, peroxidase, and esterase isozyme patterns.

The heterokaryotic strains produced as described in Example 1 and isolated in Example 2 have a number of advantages over existing commercial mushroom strains (such as *A. bisporus* strain M8), including:

1. Very rapid colonization of mushroom compost. Whereas strain M8 is usually expected to require about 13 days of "spawn run" prior to casing, strain H1-041 can be cased after 9-10 days or even earlier.

2. Lack of "scaley" mushrooms in first break. Strain M8 has the negative characteristic of having scaley first-break mushrooms. The H1-SSI strains (especially strain H1-041) have smooth, white mushrooms consistently throughout the crop.

3. Yields of H1-SSI strains (especially H1-041) are equivalent to strain M8. In some tests, strain H1-041 produced significantly higher yields.

4. The H1-SSI strains are tolerant of higher temperatures than strain M8 or other *A. bisporus* strains. While strain M8 is adversely affected by temperatures above 29°-30° C., H1-SSI strains (especially strain H1-041) can tolerate temperatures in the range of 32°-33° C. This trait will be beneficial to some commercial mushroom farms with high summer air temperatures but inadequate or marginally adequate cooling capacity.

One of thes strains, with the internal designation H1-041, has been deposited with the American Type Culture Collection, Rockville, Md., on Jan. 13, 1989, and given the accession number ATCC 20917.

Although preferred embodiments of the invention have been discussed herein, those skilled in the art will appreciate that changes and modifications may be made without departing from the spirit of this invention, as defined in and limited only by the scope of the appended claims. For example, those skilled in the art of propagating commercial mushrooms will be able to perform similar matings using the interspecies strain HB3 provided through this invention, or its progeny, as one parent to obtain heterokaryotic mushroom strains with beneficial traits from all of the species included in their parentage. These beneficial traits would be unattainable in the absence of the interspecies strain provided by this invention.

I claim:

1. A strain of the genus Agaricus which has the distinguishing characteristics of the strain deposited with the American Type Culture Collection under accession number 20916.

2. A strain of the genus Agaricus which has the distinguishing characteristics of the strain deposited with the American Type Culture Collection under accession number 20917.

* * * * *